United States Patent
Bassin

(10) Patent No.: US 8,256,418 B2
(45) Date of Patent: Sep. 4, 2012

(54) DETERMINATION OF LEAK DURING CPAP TREATMENT

(75) Inventor: David John Bassin, Coogee (AU)

(73) Assignee: ResMed Limited (AU)

( * ) Notice: Subject to any disclaimer, the term of this patent is extended or adjusted under 35 U.S.C. 154(b) by 501 days.

(21) Appl. No.: 12/438,758

(22) PCT Filed: Aug. 30, 2007

(86) PCT No.: PCT/AU2007/001237
§ 371 (c)(1),
(2), (4) Date: Feb. 25, 2009

(87) PCT Pub. No.: WO2008/025064
PCT Pub. Date: Mar. 6, 2008

(65) Prior Publication Data
US 2010/0101574 A1    Apr. 29, 2010

(51) Int. Cl.
*F16K 31/02* (2006.01)
(52) U.S. Cl. .......... 128/204.21; 128/204.22; 128/204.23
(58) Field of Classification Search ............ 128/202.22, 128/204.18, 204.21–204.23
See application file for complete search history.

(56) References Cited

U.S. PATENT DOCUMENTS

| 6,152,129 | A | 11/2000 | Berthon-Jones |
| 6,659,101 | B2 * | 12/2003 | Berthon-Jones ......... 128/204.21 |

FOREIGN PATENT DOCUMENTS

| DE | 10023473 | 12/2001 |
| EP | 714670 | 6/1996 |
| EP | 1005829 | 6/2000 |
| EP | 1005830 | 6/2000 |
| WO | 98/12965 | 4/1998 |

OTHER PUBLICATIONS

Chinese Application No. 200780031961.7, Office Action, Feb. 17, 2011, Chinese Patent Office.

* cited by examiner

*Primary Examiner* — Glenn Richman
(74) *Attorney, Agent, or Firm* — Lerner, David, Littenberg, Krumholz & Mentlik, LLP

(57) ABSTRACT

In a CPAP or positive pressure ventilation system, leak is determined at each instant by a lookback for a time as long as single breath to establish the start of an averaging window over which low-pass filtered values used in the determination of a parameter of a leak model are averaged. A jamming index indicates whether the leak is rapidly changing. To the extent that jamming is high, the leak estimate used progressively changes from that using sliding breath-window averaging to a more robust and faster responding low-pass filter method, and adjustment of ventilatory support based on measures employing estimated respiratory flow is slowed down or stopped.

8 Claims, 2 Drawing Sheets

Figure 1A:
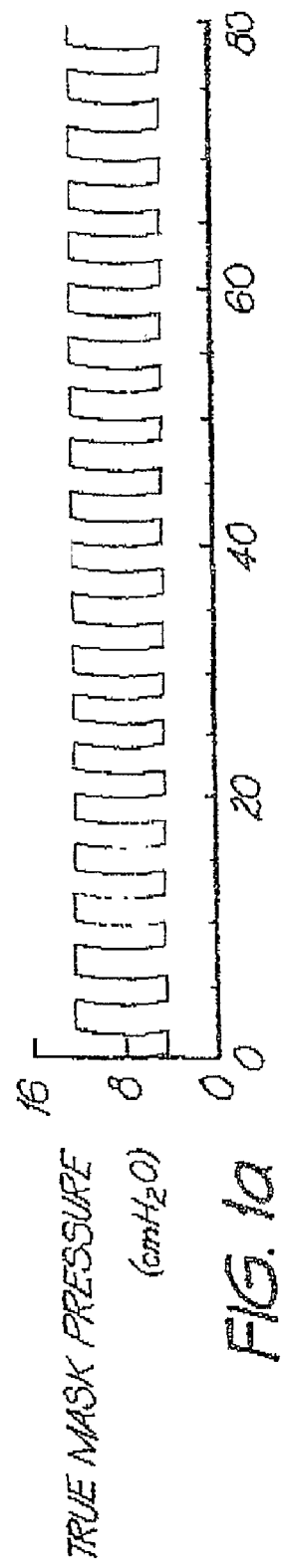

MEASURED MASK FLOW
(L/sec)

CALCULATED LEAK
(L/sec)

CALCULATED RESP. AIRFLOW
(L/sec)

DETERMINATION OF LEAK DURING CPAP TREATMENT

FIELD OF THE INVENTION

This invention relates to treatment of apneas and other respiratory disorders. In particular it relates to methods and apparatus for the determination of leakage airflow and true respiratory airflow, during the mechanical application of positive airway pressure.

BACKGROUND OF THE INVENTION

For the treatment of apneas and other respiratory disorders, breathable gas is supplied from a mechanical respirator or ventilator, for example via a mask, at a pressure which may be higher during inspiration and lower during expiration. (In this specification any reference to a "mask" is to be understood as including all forms of devices for passing breathable gas to a person's airway, including nose masks, nose and mouth masks, nasal prongs/pillows and endotracheal or tracheostomy tubes. The term "ventilator" is used to describe any device that does part of the work of breathing.) Typically one measures the subject's respiratory airflow during mechanical ventilation to assess adequacy of treatment, or to control the operation of the ventilator.

Respiratory airflow is commonly measured with a pneumotachograph placed in the gas delivery path between the mask and the pressure source. Leaks between the mask and the subject are unavoidable. The pneumotachograph measures the sum of the respiratory airflow plus the flow through the leak plus flow through the vent (also called "deliberate leak"). If the instantaneous flow through the leak is known, the respiratory airflow can be calculated by subtracting the flow through the leak and the flow through the vent from the flow at the pneumotach. Typically the flow through the vent is a known function of pressure at the vent, and given that the pressure at the vent can be estimated with reasonable accuracy, the flow through the vent can then be straightforwardly calculated. On the other hand, if the vent characteristics are suitable for the leak model employed, the vent flow and non-deliberate leak can be lumped together and estimated as a single quantity. The direct estimation of vent flow using pressure at the vent will be assumed hereinafter, and subtraction of this vent flow from total ventilator outflow will be assumed to have occurred when not mentioned explicitly.

Some methods to correct for the flow through the leak assume (i) that the leak is substantially constant, and (ii) that over a sufficiently long time, inspiratory and expiratory respiratory airflow will cancel. If these assumptions are met, the average flow through the pneumotach over a sufficiently long period will equal the magnitude of the leak, and the true respiratory airflow may then be calculated as described.

The known method is only correct if the pressure at the mask is constant. If, on the other hand, the mask pressure varies with time (for example, in the case of a ventilator), assumption (i) above will be invalid, and the calculated respiratory airflow will therefore be incorrect. This is shown markedly in FIGS. 1a-1f.

Figure 1B:
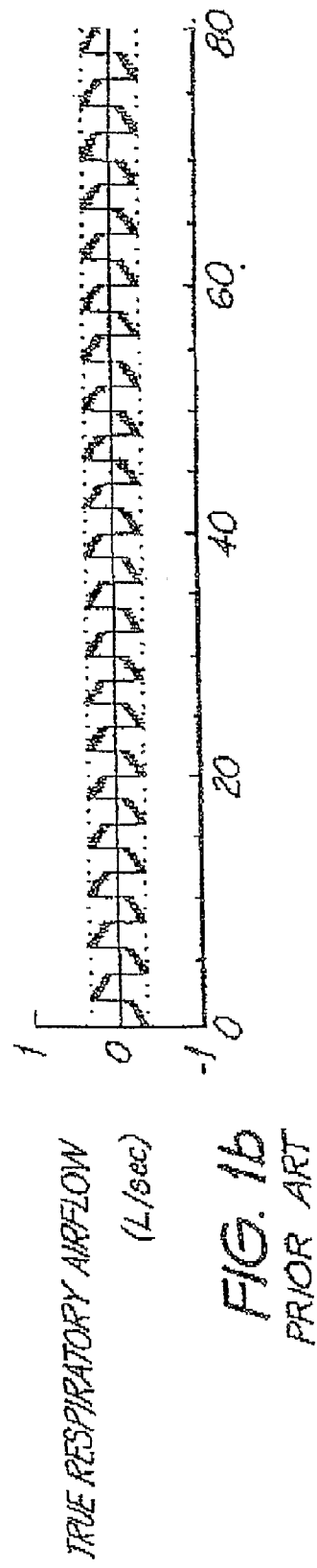
Figure 1C:
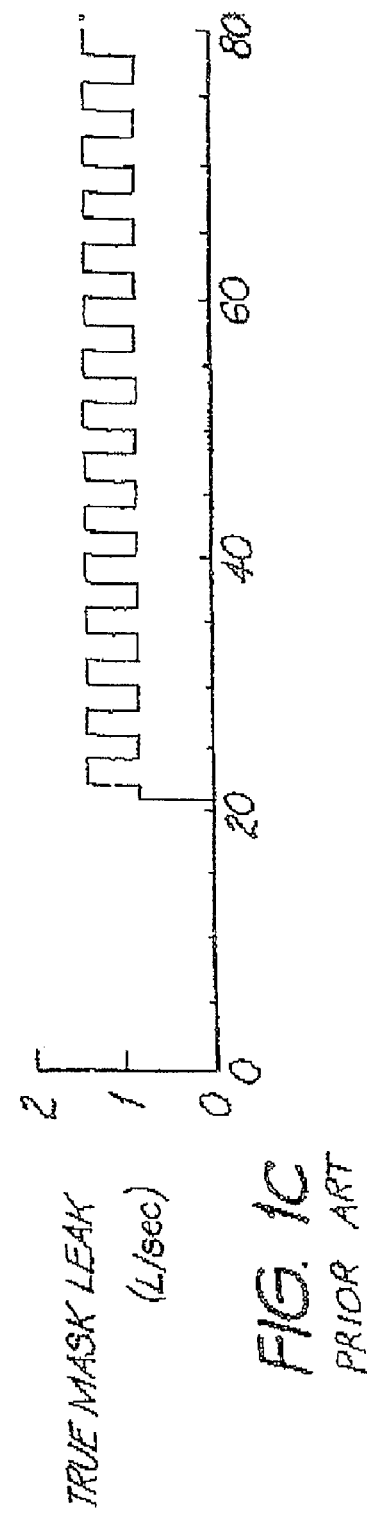
Figure 1D:
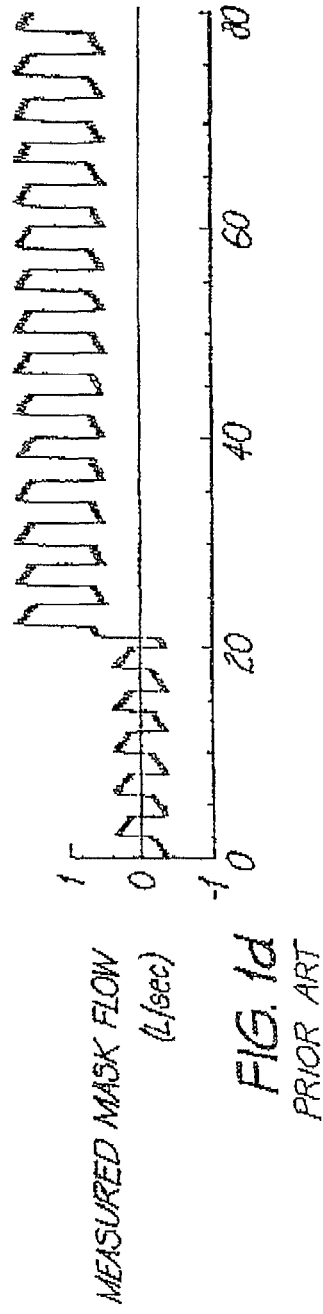
Figure 1E:
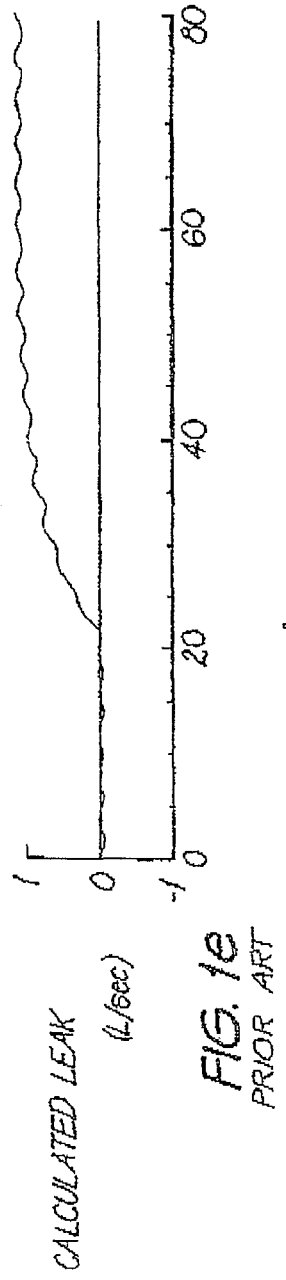
Figure 1F:
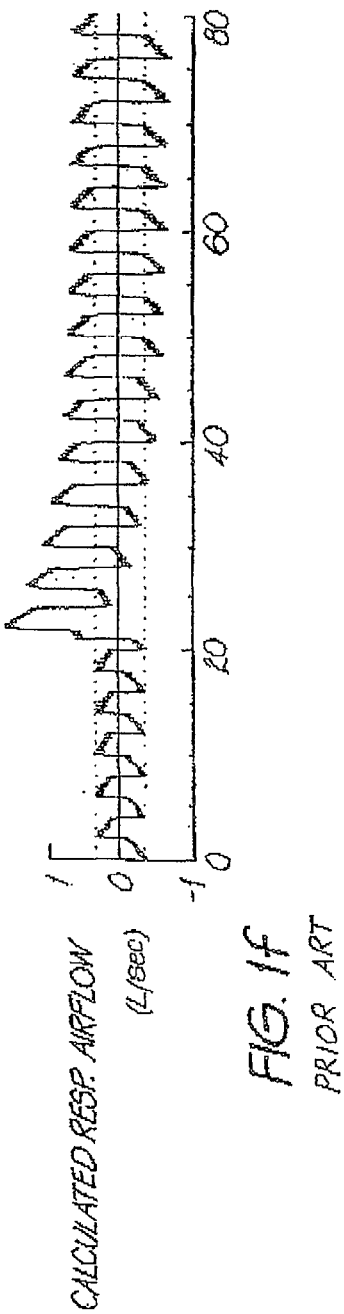

FIG. 1a shows a trace of measured mask pressure in bi-level CPAP (Continuous Positive Airway Pressure) treatment between about 4 cm $H_2O$ on expiration and 12 cm $H_2O$ on inspiration. FIG. 1b shows a trace of true respiratory airflow in synchronism with the mask pressures. At time=21 seconds a mask leak occurs, resulting in a leakage flow from the leak that is a function of the treatment pressure, as shown in FIG. 1c. The measured mask flow shown in FIG. 1d now includes an offset due to the leak flow. The prior art method then determines the calculated leak flow over a number of breaths, as shown in FIG. 1e. The resulting calculated respiratory flow, as the measured flow minus the calculating leak flow is shown in FIG. 1f, having returned to the correct mean value, however is incorrectly scaled in magnitude, giving a false indication of peak positive and negative airflow.

Another prior art arrangement is disclosed in European Publication No. 0 714 670 A2, including a calculation of a pressure-dependent leak component. The methodology relies on knowing precisely the occurrence of the start of an inspiratory event and the start of the next inspiratory event. In other words, the leak calculation is formed as an average over a known breath and applied to a subsequent breath.

This method cannot be used if the moment of start and end of the previous breath are unknown. In general, it can be difficult to accurately calculate the time of start of a breath. This is particularly the case immediately following a sudden change in the leak.

Furthermore, the method will not work in the case of a subject who is making no respiratory efforts, and is momentarily not being ventilated at all, for example during an apnea, because for the duration of the apnea there is no start or end of breath over which to make a calculation.

In U.S. Pat. No. 6,162,129 (Berthon-Jones) the leak is determined by first estimating the conductance of the leak path from the longterm orifice flow:

$$\frac{1}{R_L} = \frac{<Q>}{<\sqrt{p}>},$$

where $G_L=1/R_L$ is conductance (L denotes leak), Q is instantaneous flow, p is instantaneous pressure and $<\ >$ denotes a longterm average calculated for example by low pass filtering with an IIF or other filter having a long time constant. Note that the word "average" as used herein contains the general sense inclusive of the result of a low pass filtering step, and is not limited to an arithmetic mean or other standard average such as the RMS average.

The instantaneous leak flow, based on the model of the flow through an orifice is then $$Q_L = \frac{1}{R_L}\sqrt{p}.$$

Note that the instantaneous respiratory airflow is then $Q_R=Q-Q_L$.

Berthon-Jones attempts to deal with sudden changes in instantaneous leak flow by dynamically adjusting the filter's time constant using fuzzy logic, lengthening the time constant if it is certain that the leak is steady, reducing the time constant if it is certain that the leak has suddenly changed, and using intermediately longer or shorter time constants if it is intermediately certain that the leak is steady.

Berthon-Jones also develops a jamming index by fuzzy logic to deal with the case of a large and sudden increase in the conductance of the leak, in which case the calculated respiratory airflow will be incorrect. In particular during apparent inspiration, the calculated respiratory airflow will be large positive for a time that is large compared with the expected duration of a normal inspiration. Conversely, if there is a sudden decrease in conductance of the leak, then during apparent expiration the calculated respiratory airflow will be large negative for a time that is large compared with the duration of normal expiration.

Therefore, the jamming index, i.e. an index of the degree of certainty that the leak has suddenly changed, is derived, such that the longer the airflow has been away from zero, and by a larger amount, the larger the index. The explicit calculation of the jamming index by fuzzy logic is described in the '129 patent, which is incorporated herein by reference.

The time constant for the low pass filters is then adjusted to vary inversely with the jamming index. In operation, if there is a sudden and large change in the leak, the index will be large, and the time constant for the calculation of the conductance of the leak will be small, allowing rapid convergence on the new value of the leakage conductance. Conversely, if the leak is steady for a long time, the index will be small, and the time constant for calculation of the leakage conductance will be large; enabling accurate calculation of the instantaneous respiratory airflow, in the spectrum of intermediate situations, where the calculated instantaneous respiratory airflow is larger and for longer periods, the index will be progressively larger, and the time constant for the calculation of the leak will progressively reduce. For example, at a moment in time where it is uncertain whether the leak is in fact constant, and the subject merely commenced a large sigh, or whether in fact there has been a sudden increase in the leak, the index will be of an intermediate value, and the time constant for calculation of the impedance of the leak will also be of an intermediate value.

BRIEF DESCRIPTION OF THE INVENTION

This invention rapidly determines the instantaneous leak in a CPAP system without detailed modeling the source of the leak and without having to determine the precise phase in a breathing cycle at which the leak occurs. It relies instead on the use of timers to define the breathing cycle and a calculation to assure that the instantaneous flow is compared to the flow over a time period long enough to include an entire breath. It does this by looking backward to include an entire phase cycle. This avoids having to take long term averages over multiple breaths, or to have a model that recognized the beginning and end of a breath.

Sudden changes in a leak are recognized and the degree to which leak is rapidly changing is expressed as a jamming index value, which is then used as a parameter to adjust the contributions of the components of which the leak estimate is made up, and, in the case of a servoventilator, to temporarily slow down or suspend the adjustment of the servoventilator controller output parameter, typically pressure support level.

DETAILED DESCRIPTION OF PREFERRED EMBODIMENTS OF THE INVENTION

The present invention is motivated by the desire to produce a continuously updated estimate of the leak model parameter which is very stable when the actual leak parameter is stable, but which degrades progressively and gracefully to a less stable, less accurate but faster-responding estimate when the actual leak parameter is changing rapidly. The leak model parameter in question is typically an orifice constant (equivalently a leak conductance), but need not be.

A continuously updated estimate of leak conductance (in particular, continuously updated during each breath) may be calculated by performing some kind of low-pass filtering operation, such as a 1st-order low pass filter or a moving average filter, typically with a fixed window length, on the non-vent flow (equal to the sum of the respiratory flow and the instantaneous leak flow) and on the square root of the mask pressure, producing a leak conductance estimate $G_1$, as in Berthon-Jones. This method has the advantage over some other methods that it is independent of the determination of breath phase (the position within the current breath). Thus sudden changes in leak can occur which cause respiratory flow estimates and hence breath phase estimates to be grossly in error, yet updating of the leak parameter estimates continues. A disadvantage of such breath-independent estimates is that the estimates are not stable within a breath unless particular fortuitous events occur; for example, by coincidence, the duration of a window averaging filter includes exactly N breaths, where N is an integer. A particular case of this instability is illustrated by considering the situation when 1st order low-pass-filter estimates of mask flow and mask pressure are used. For simplicity, assume that a mask pressure is constant, and that true leak conductance is zero. Then the leak flow estimate is just a 1st-order low-pass-filtered version of respiratory flow. This estimate rises whenever respiratory flow is above the leak flow estimate, and falls when respiratory flow is below the leak flow estimate. In particular, with reasonable filter time constants, the leak flow estimate rises during most of inspiration and falls during most of inspiration, rising slowly during the expiratory pause, and under normal circumstances crucially being below zero during the expiratory pause. Since true respiratory flow is zero during the expiratory pause, estimated respiratory flow, being the difference between mask flow (by assumption equal to respiratory flow) and estimated leak flow, is positive during the expiratory pause, say equal to $Q_{eps}$. If a ventilator is designed to trigger into inspiration when the estimated respiratory flow exceeds some true respiratory flow threshold $Q_{insp\_thresh}$, a ventilator which uses this kind of leak estimate, in order to trigger at the desired true respiratory flow, must set its trigger threshold to a higher value $Q_{insp\_thresh}+Q_{eps}$. Unfortunately $Q_{eps}$ is a function of the respiratory flow shape, the respiratory rate, and the low-pass-filter time constant, very difficult if not impossible to determine in real time. Hence triggering actually occurs at a variable threshold, and in the worst case auto-triggering (triggering at a true respiratory flow of zero) may occur. It should be noted that the effect of the non-constant estimate of leak parameter in producing a distorted respiratory flow exists throughout the breath and whether there is an identifiable expiratory pause or not, with potential adverse effects on cycling (expiratory triggering) as well an on (inspiratory) triggering, as well as other algorithms which operate on estimated respiratory flow.

"Jamming", as described by Berthon-Jones, is the extent to which the leak has not yet been compensated for, and usually results from a rapid change in the leak. It is herein considered to be a fuzzy logical quantity.

A leak conductance estimate $G_1$ is calculated as described above. Note that the time constant of the filters uses preferably decreases as jamming increases, as described in Berthon-Jones.

A second leak conductance estimate $G_2$ is calculated continuously, at the algorithmic sampling frequency or a lower frequency (e.g. 10 Hz) which is still high compared with the respiratory frequency. In a manner described below, the algorithm identifies the position in the current breath, then attempts to find time associated with the same position in the preceding breath. If it fails to find such a position, it uses instead a time 10 seconds in the past. Between that time in the past and the present, a window is established. Low-pass filtered mask flow and low-pass filtered square root of mask pressure (filtered by a non-breath-dependent method, such as a 1st-order LPF), typically the low-pass filtered values used for the determination of $G_1$, are then further low-pass filtered by being averaged over this window. The ratio of these window-averaged values is the leak conductance estimate $G_2$, which under conditions of stable leak is extremely stable.

Because $G_2$ responds rather slowly to changes in leak conductance, it is inappropriate to use when the leak is changing rapidly. Thus to the extent that there is jamming, $G_1$ rather than $G_2$ is used. In the preferred implementation, if J is jamming (a quantity in [0,1]), the conductance estimate $G_j$ is used, given by $$G_j = JG_1 + (1-J)G_2$$

Instantaneous leak is then straightforwardly calculated by $Q_{leak} = G_j\sqrt{P_{mask}}$.

Determining the Position of the Start of the Averaging Window for $G_2$

The aim is to determine the same position in the previous breath as the patient, is at in the current breath. For this one needs a concept of breath phase which is not just one of a small set of categories, such as inspiration and expiration, but a conceptually real-valued (in practice rational) variable which increases progressively from the start of inspiration to the end of expiration, potentially with a small finite number of jumps. Such a concept is provided in Berthon-Jones Cheyne-Stokes patent, WO98/012065, which is incorporated herein by reference. Breath phase is there defined to be 0 at the start of inspiration, 0.5 at the start of expiration, and approaches 1 at the end of expiration. Given such a breath phase, one find the breath phase at the current moment, then searches backward in time to find the same breath phase in the previous breath. Because breath phase as estimated by the system described by Berthon-Jones is not necessarily increasing with time during a breath (neglecting the expiratory to inspiratory transition, at which it must decrease) though typically it is increasing with time during a breath, it is necessary to have an algorithm which searches backward in time in such a way that a point in the same breath with the same breath phase as the current value is not identified as being in the previous breath. Such a search algorithm is described below; this algorithm may fail under exceptional circumstances, but is quite robust most of the time. Because of jumps in phase, there may exist no point in the previous breath with a phase equal to the phase associated with the current moment, the latest time in the previous breath with a phase less than or equal to the phase at the current moment is used instead.

On the other hand, a system which uses conventional flow thresholds for triggering and cycling need not use a fuzzy logical system for determining breath phase for the purpose of finding the same position in the previous breath as in the current breath. Assuming that during inspiration, the maximum time between the present until the end of inspiration is known (typically determined at the start of inspiration, but not necessarily), the breath phase at each sampling interval is increased by such an amount that with equal increments of that amount, the phase would reach 0.5 at the end of inspiration. For example, in the simple case where a maximum inspiratory time of 1.6 seconds was determined at the start of inspiration, the phase would increase at a steady rate of 0.5/1.6 phase units/second. If cycling (transition to expiration) occurred earlier, for example because respiratory flow fell below a cycling threshold, the phase would at that point jump to 0.5. Similar considerations apply during expiration, with rate of increase of phase being the difference between 1 and the current phase divided by the time remaining until the maximum expiratory time. If Since breath phase determined in this way is typically used only for the purpose of determining the same position in the previous breath as in the current breath, it is called "book-keeping" phase.

Regardless of the phase determination method used, whether that of Berthon-Jones, "book-keeping" phase as described above, or some other method, the search backward in time to find the latest time in the preceding breath with a phase less than or equal to the phase at the current moment is performed as follows (though it will be appreciated that for "book-keeping" phase, simpler methods are available).

Starting with the current phase, say $\phi_0$, the invention looks backwards in time for the most recent phase in the interval $[\phi_0-0.75, \phi_0-0.25]$. The aim is to seek a point in time at least 0.25 of a breath before the present. When such a phase is found, the invention calculates $\phi_1 = \phi_0 - 0.25$ and looks backward for a phase in the interval $[\phi_1-0.75, \phi_1-0.25]$. This is continued, 0.25 at a time, i.e. $\phi_{i+1} = \phi_i - 0.025$. When a phase is found which is in $[\phi_3-0.075, \phi_3-0.25]$ the iteration ceases, since this is just $[\phi_0-0.5, \phi_0]$. If phase varied continuously this would have found exactly $\phi_0$; in reality it will most likely find $\phi_0 - \epsilon$, where hopefully $\epsilon$ is small. By proceeding in this manner we have some confidence that the phase has gone backward rather than forward, since we have found phases in the 4 phase quadrants before the present. This algorithm will regard two phase transitions of 0.5 in succession as being movement backward, though the actual direction is of course actually indeterminate. If this algorithm fails to find a point between the present moment and a time before the present which meets this criterion, we take the start of the averaging window to be some reasonable maximum time before the present, such as 10 seconds. As an implementation detail, to reduce computational requirements, the leak, flow values may be averaged over the last 0.1 seconds and stored in a buffer accompanied by the associated breath phase, so that the search for the last breath is performed in a buffer of 100 points, and done every 0.1 seconds. The averaged leak estimate at the instantaneous leak calculation frequency, e.g. 100 Hz, can then be calculated by linear interpolation between the most recent averaged leak conductance estimate and the averaged conductance leak estimate just before it.

in a servoventilator or other system using some kind of measure of ventilation (such as half the absolute value of respiratory flow, or a gross alveolar ventilation, or peak flow, or some weighted average of flows determined during inspiration or expiration) to adjust ventilatory support, when jamming is observed, the system slams down or suspends changes in pressure support. This is because respiratory flow estimates are not reliable in the presence of jamming, and various measures of ventilation based on respiratory flow are likely to overestimate ventilation, leading for example in a servoventilator to unwarranted withdrawal in ventilatory support because ventilation appears to be above target ventilation. The extent of slowing down of adjustment of respiratory support is preferably some increasing function of the jamming. For example, if the calculated change in respiratory support from that at the previous time that it was calculated is some value $\Delta S$, then the adjusted change in support would be $k \Delta S$, where for example k is 1 for $J \leq 0.1$, 0 for $J \geq 0.3$, and taking linearly interpolated values for intermediate values of J.

What is claimed is:
1. A method of determining a mask leak conductance in a patient respiratory device, comprising:
   determining a first estimate of leak conductance which responds relatively quickly to changes in leak conductance, determining a second estimate of leak conductance which responds more slowly to changes in leak conductance, and determining the mask leak conductance as a function of the first and second estimates of leak conductance.

2. A method according to claim 1, further comprising determining the pressure in the mask.

3. A method according to claim 2, further comprising determining an estimate of non-deliberate mask leak as a function of the mask leak conductance and the mask pressure.

4. A method according to claim 3, wherein the non-deliberate mask leak is calculated as:

$$Q_{leak} = G_j \sqrt{P_{mask}}$$

wherein:
$Q_{leak}$ is non-deliberate mask leak,
$G_j$ is mask leak conductance, and
$P_{mask}$ is mask pressure.

5. A method according to claim 1, further comprising determining an uncompensated leak index representative of an extent to which mask leak is uncompensated.

6. A method according to claim 5, wherein the mask leak conductance is calculated as a function of the uncompensated leak index and the first and second estimates of leak conductance.

7. A method according to claim 6, wherein the mask leak conductance is calculated as:

$$G_j = JG_1 + (1-J)G_2$$

wherein:
$G_j$ is an estimate of mask leak conductance,
$G_1$ is the first estimate of leak conductance.
$G_2$ is the second estimate of leak conductance, and
J is a jamming index of the uncompensated mask leak.

8. A method of claim 7, wherein the jamming index is between zero and one.

* * * * *